(12) United States Patent
Frech

(10) Patent No.: US 7,533,758 B1
(45) Date of Patent: May 19, 2009

(54) APPARATUS AND METHOD FOR AUSCULTATION AND PERCUSSION OF A HUMAN OR ANIMAL BODY

(76) Inventor: Abraham Jacobo Frech, 26 Tamarac Pl., Aliso Viejo, CA (US) 92656

( * ) Notice: Subject to any disclaimer, the term of this patent is extended or adjusted under 35 U.S.C. 154(b) by 607 days.

(21) Appl. No.: 11/220,168

(22) Filed: Sep. 6, 2005

Related U.S. Application Data

(60) Provisional application No. 60/608,224, filed on Sep. 8, 2004.

(51) Int. Cl.
*A61B 7/02* (2006.01)
*A61B 5/02* (2006.01)

(52) U.S. Cl. .................. 181/131; 600/553; 600/528; 606/238

(58) Field of Classification Search .............. 181/131; 600/552, 559, 586, 553, 528; 128/897; 381/67; 606/238
See application file for complete search history.

(56) References Cited

U.S. PATENT DOCUMENTS

| | | | | |
|---|---|---|---|---|
| 2,048,220 | A * | 7/1936 | Redding | 606/238 |
| 2,800,895 | A * | 7/1957 | Torricelli | 600/553 |
| 3,247,324 | A | 4/1966 | Cefaly et al. | |
| 3,653,373 | A * | 4/1972 | Batterman | 600/586 |
| 3,722,100 | A * | 3/1973 | Weisman et al. | 433/72 |
| 3,774,598 | A * | 11/1973 | Wilson et al. | 601/27 |
| 4,669,454 | A * | 6/1987 | Shamos | 606/238 |
| 5,003,605 | A | 3/1991 | Phillipps et al. | |
| 5,458,118 | A * | 10/1995 | Monsivais | 600/553 |
| 5,548,651 | A | 8/1996 | Long | |
| 5,931,792 | A * | 8/1999 | Packard et al. | 600/528 |
| 5,960,089 | A | 9/1999 | Bouricius et al. | |
| 6,485,434 | B1 | 11/2002 | Kahana et al. | |
| 6,510,918 | B2 * | 1/2003 | Bates | 181/131 |
| 6,723,060 | B2 * | 4/2004 | Miller | 601/101 |
| 6,790,184 | B2 | 9/2004 | Thierman | |
| 6,966,400 | B1 * | 11/2005 | Rollins et al. | 181/131 |
| 7,285,098 | B2 * | 10/2007 | Thierman | 600/553 |
| 7,314,112 | B1 * | 1/2008 | Rollins et al. | 181/131 |
| 7,393,326 | B2 * | 7/2008 | Bindefeld | 600/453 |
| 2002/0058889 | A1 | 5/2002 | Lee | |
| 2007/0181053 | A1 * | 8/2007 | Gray | 116/59 |
| 2007/0250117 | A1 * | 10/2007 | Kwong | 606/219 |

FOREIGN PATENT DOCUMENTS

| | | |
|---|---|---|
| DE | 004231629 | 5/1993 |
| DE | 10320011 A1 * | 12/2002 |
| RU | 2012233 C * | 5/1994 |

* cited by examiner

*Primary Examiner*—Edgardo San Martin
(74) *Attorney, Agent, or Firm*—Egbert Law Offices PLLC

(57) ABSTRACT

An apparatus for auscultation and percussion of a human or animal body has a stethoscope with a diaphragm on one side of a head thereof, and a percussion mechanism positioned in the head for selectively producing a percussion against the body such that a sound from the percussion mechanism is passed through a tube connected to the head. The percussion mechanism includes a cylinder positioned within the head, a piston slidably positioned within the cylinder, and an activator lever connected to the piston for moving the piston between a first position adjacent to an impact element and a second position away from the impact element.

15 Claims, 3 Drawing Sheets

APPARATUS AND METHOD FOR AUSCULTATION AND PERCUSSION OF A HUMAN OR ANIMAL BODY

RELATED U.S. APPLICATIONS

The present application claims priority from a Provisional Application by the same inventor, having U.S. Ser. No. 60/608,224, filed on Sep. 8, 2004 and entitled "APPARATUS AND METHOD FOR ALLOWING SIMULTANEOUS AUSCULTATION AND PERCUSSION OF A HUMAN OR ANIMAL BODY".

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to stethoscopes. More particularly, the present invention relates to stethoscopes that produce percussion against the human body. Furthermore, the present invention relates to stethoscopes that allow for simultaneous auscultation and percussion.

BACKGROUND OF THE INVENTION

Auscultation is defined as listening to the sounds made by various body structures as a diagnostic method. Auscultation can be used to listen to the patient's lungs, heart, intestines, and blood vessels in order to evaluate the frequency, intensity, duration, number and quality of sounds. Percussion is a diagnostic technique designed to determine the density of a body part by the sound produced by tapping the surface with the finger or a plessor. Percussion is usually performed over the chest in order to determine the presence of normal air content in the lungs and over the abdomen in order to evaluate air in the loops of the intestine and the size of solid organs, such as the liver and spleen. Percussion is also a form of massage consisting of repeated blows or taps of varying forces.

Good percussion technique can involve the hyperextension of the middle finger of a hand, known as the pleximeter finger. The distal interphalangeal joint is firmly pressed on the surface to be percussed. Surface contact should be avoided by any other part of the hand since other surface contact tends to dampen out vibrations. The forearm of the other arm is positioned close to the surface with the hand cocked upwardly. The middle finger should be partially flexed, relaxed and poised to strike. The pleximer finger is struck with the middle finger (or plexor finger) of the other hand with a quick, sharp, but relaxed, wrist motion. The aim is toward the distal interphalangeal joint. The strike occurs with the tip of the plexor finger and not the finger pad. The finger should be almost at a right angle to the pleximeter. The striking finger should be withdrawn quickly in order to avoid the vibrations created thereby.

Manual percussion has several disadvantages. In order to perform the percussion correctly, the examiner should have satisfactory coordination in order to apply a force to a location that is the thickness of a finger. Even when performed correctly, the sounds produced by percussion may not be clear to the examiner. Manual percussion may also become increasingly difficult to perform and less accurate when examining certain parts of the body, when examining from particular angles, or in the examination of obese patients.

Stethoscopes have various designs. In the medical field, stethoscopes traditionally have two sides on its head, a diaphragm side for high frequency sounds and bell side for low frequency sounds. Stethoscopes have also been designed so as to have both diaphragm and bell combined on one side. Currently, stethoscopes are used to auscultate a body. There are no stethoscopes that function effectively as percussion instruments.

Percussion devices also have various designs. Some percussion devices are as simple as a percussion hammer. Other percussion devices utilize sophisticated systems in order to produce sound that can be manipulated and monitored by way of a speaker. No percussion device has heretofore been contained within the head of a stethoscope.

U.S. Pat. No. 6,790,184, issued on Sep. 14, 2004 to J. S. Thierman, discloses a mechanical tapper that clips onto the end of the stethoscope. This mechanism has several disadvantages. Since it is an attachment, this device is not designed for simultaneous percussion and auscultation. As an attachment to the stethoscope, the percussion sounds obtained by the apparatus will refer to an area in the vicinity of the stethoscope and do not refer to the area below the center of the diaphragm of the stethoscope. The sounds produced by such a mechanism do not parallel those of manual percussion. In manual percussion, the examiner does not tap directly on the body, but rather the examiner taps on a finger that is firmly placed on the body to be examined. The tapper should not make contact directly with the body but rather should tap on some surface, such as rubber in order to mimic the examiner's fingers. This may not only produce inappropriate sound, but may also cause the patient discomfort by tapping directly on the body surface. The method of this patent does not disclose the technique whereby percussion sounds travel directly into the stethoscope. This attachment can only transmit sounds by way of the diaphragm. Since the methods in which the sounds are produced and transmitted are somewhat flawed, the examiner will not hear the same sound as heard during manual percussion. The attachment system mates with the head of the stethoscope and, as a result, the attachment may be inconvenient for both the examiner and the patient, especially when examining certain parts of the body. The attachment would not allow the examiner to percuss beyond certain angles since it is fixed on a 180° plane with respect to the diaphragm of the stethoscope. The apparatus of this patent does not disclose the use of a force that can be increased or decreased in order to accommodate different body wall thicknesses nor does it disclose a method of detachment wherein the device may be used separately as a percussion apparatus.

Various other U.S. patents have related to such diagnostic techniques. For example, U.S. Pat. No. 3,247,324, issued on Apr. 19, 1966 to R. Cefaly et al., teaches an acoustic and electronic stethoscope which includes a microphone and an amplifier for enhancing the receipt of acoustic signals from the human body.

U.S. Pat. No. 5,003,605, issued on Mar. 26, 1991 to Phillipps et al., discloses a stethoscope that simultaneously provides the listener with combined unmodified, familiar audible sounds along with sounds that have been electronically augmented to bring them within the human auditory range. A timing sound is provided along with the unmodified, familiar audible sounds and electronically augmented sounds in order to assist the listener in determining when sound occurs in the heart cycle.

U.S. Pat. No. 5,548,651, issued on Aug. 20, 1996 to H. F. Long, discloses a stereophonic stethoscope that utilizes binaural phase effect from two probes held in one chestpiece with an amplifier. The skin contacts in the probes are small in order to fit body curves and spread for wide pickup.

U.S. Pat. No. 5,960,089, issued on Sep. 8, 1999 to Bouricius et al., provides an ultrasound bell attachment for a stethoscope. The ultrasound bell includes an ultrasound transmitter for emitting ultrasound acoustic waves or signals and an ultrasound sound detector for receiving the reflected waves and converting these waves into electrical signals. The electronic circuitry within the ultrasound bell converts the electric signals created by the ultrasound detector into sound waves emitted by a speaker. The speaker is acoustically coupled to the turret of the acoustic stethoscope such that an airtight acoustic wave pathway is formed between the ultrasound bell and the turret of the stethoscope.

U.S. Pat. No. 6,485,434, issued Nov. 26, 2002 to Kahana et al., discloses an apparatus for acoustic percussion of a body. This apparatus has an oscillator circuit for creating electrical waves for exciting a loudspeaker and producing sound waves. A waveform shaping circuit shapes the electrical signals created by the oscillator into a waveform. A loudspeaker produces sound waves when excited by the electrical signals created by the oscillator. A potentiometer controls the tone produced by the oscillator and controls the volume of the sound.

U.S. Patent Publication No. 2002/0058889, published on May 16, 2002 to B. H. Lee, describes an automatic diagnostic apparatus with a stethoscope. In this device, the name of a disease is automatically determined and recorded based upon the auscultated sounds. The waveforms of the auscultated sounds from the stethoscope are converted into digital data and inputted into a computer. These digital data signals are compared with standard data that have been inputted into the computer in advance. As a result, a diagnosis of the disease is automatically provided.

German Patent No. DE004231629, published on May 13, 1993, discloses a method for analyzing the frequency characteristics of a heart. This method analyzes typical amplitude behavior with the percussion of the lungs for providing diagnosis through an audio/visual stethoscope.

It is an object of the present invention to provide an apparatus and method for providing simultaneous auscultation and percussion of a human or animal body.

It is still a further object of the present invention to provide a stethoscope apparatus that provides the examiner with the ability to auscultate and percuss simultaneously.

It is another object of the present invention to provide an apparatus which decreases physical examination time and provides increased comfort for the patient.

It is another object of the present invention to provide an apparatus which gives the examiner clear percussion sounds by way of the stethoscope.

It is still a further object of the present invention to provide an apparatus that allows percussion on the body to occur where manual percussion is difficult, inaccurate, unreliable or inefficient.

It is still a further object of the present invention to provide an apparatus which allows for percussion to occur from various angles of the body or in association with obese patients.

It is still another object of the present invention to provide an apparatus which provides simultaneous auscultation and percussion which is simple, reliable and cost-effective.

It is a further object of the present invention to provide an apparatus which allows for simultaneous auscultation and percussion in a device that has minimal moving parts and does not necessarily require an energy source to be operational.

These and other objects and advantages of the present invention will become apparent from a reading of the attached specification and appended claims.

BRIEF SUMMARY OF THE INVENTION

The present invention is a percussing stethoscope that aids an examiner during a physical examination and allows the examiner the option of carrying out simultaneous auscultation and percussion.

The apparatus of the present invention comprises a stethoscope with a percussing means positioned within its head. The head consists of a diaphragmatic side and a bell side. The diaphragmatic side contains a surface for auscultation, known as the diaphragmatic surface. This surface may bend from a downward (first or "home") position to an upward (second) position. The head also contains a turret from which a passageway (in the form of tubes) connects the head to a set of ear pieces.

The percussing means is selectively producing percussion against the body such that a sound from the percussion is passed from within the percussing means through the tube and terminating at the ears of the examiner. The percussing means of the present invention serves to produce an impact against a surface, such that the two elements involved in the impact (motion-dependent impact element and motion-independent impact element) produce a sound comparable to that of a manual percussion. Although the present invention describes the impact elements as being contained within the percussion apparatus, the diaphragmatic surface may be modified to receive the impact and thus may replace the motion-independent impact element.

In the present invention, the percussion means comprises a cylinder positioned within the head and extending to the diaphragm. The cylinder includes an outer cylinder and an inner cylinder positioned inside of the outer cylinder. The cylinder is positioned such that the bottom part of the outer cylinder does not make contact with the diaphragm surface while in the auscultation mode (diaphragmatic surface in first position) but makes contact with the diaphragm surface while in percussion mode (diaphragmatic surface in second position). A fixation member extends across the outer cylinder. The inner cylinder is affixed to this fixation means. An annulus is defined in the area between the inner and outer cylinder so provide an air passage therethrough. An axle extends across the interior of the outer cylinder. A pulley is rotatably mounted to the axle. A lever extends radially outwardly of the pulley. A flexible member in the form of a wire has one end connected to a surface of the pulley and an opposite end connected to a surface of a piston opposite the surface of the diaphragm. The piston is slidably received within the inner cylinder. A spring extends through the inner cylinder. The spring has an end bearing against the fixation means and the other end bearing against the piston. The flexible member extends from the pulley through an interior of the spring. At the bottom end of the outer cylinder there is a fixed rubber element that receives the impact produced by the piston.

The percussion means thus comprises a piston (motion-dependent impact element) slidably positioned within the inner cylinder, and an activating means connected to the piston. The activating means serves to move the piston between a first ("home") position adjacent to a rubber element (motion-independent impact element) and a second position away from the rubber element. Returning back to the first position from the second position allows the piston to impact the surface of the rubber element and thus produce a sound. The diaphragm has a surface formed thereon suitable for being placed against the body. The activating means further comprises a lever mounted on a pulley such that it extends radially outward. A flexible member is affixed to the pulley at one end and affixed to the piston at the opposite end, and a spring extending in the cylinder and connected to the piston so as to urge the piston downward toward the rubber element.

In the present invention, a diaphragm deactivating means is affixed to the head for selectively deactivating the diaphragm. In particular, this diaphragm deactivating means includes a plunger resiliently mounted on the diaphragmatic side of head, and an air hole located beneath the plunger and a passageway (tube) extending from the air hole to a turret. The plunger is movable between a first ("home") position opening the air hole and a second position locking the air hole.

In the present invention, a head has a bell extending upwardly from the diaphragm. The bell has a recessed area formed inwardly of an outer edge at an end opposite the diaphragm. The lever extends into the recessed area and inwardly of the outer edge.

Due to the variety of stethoscope designs, and the various methods of achieving percussion, the dimensions, locations, and types of the elements involved in the present invention, may vary within the scope of the present invention.

The present invention allows an examiner the ability to auscultate and percuss simultaneously by using the stethoscope.

DETAILED DESCRIPTION OF THE INVENTION

Figure 1:
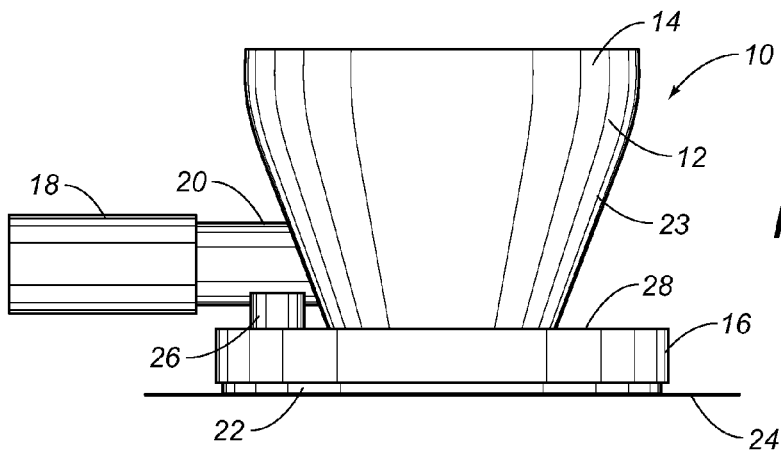
FIG. 1 is a side view of the stethoscope apparatus of the present invention.

Referring to FIG. 1, there is shown the stethoscope apparatus 10 in accordance with the preferred embodiment of the present invention. The stethoscope apparatus 10 includes a stethoscope 12 having a head 14 including a bell 23 and a diaphragm 16. A tube 18 is connected by a turret 20 to the head 14. The diaphragm 16 includes a diaphragmatic surface 22 affixed to a side of the diaphragm 16 opposite the bell 23 of the head 14. The diaphragmatic surface 22 is suitable for being placed against the surface of a body 24 of a human or animal. A diaphragm deactivating device 26 extends outwardly of a side 28 of the diaphragm 16 and is suitable for deactivating the diaphragm 16.

Figure 2:
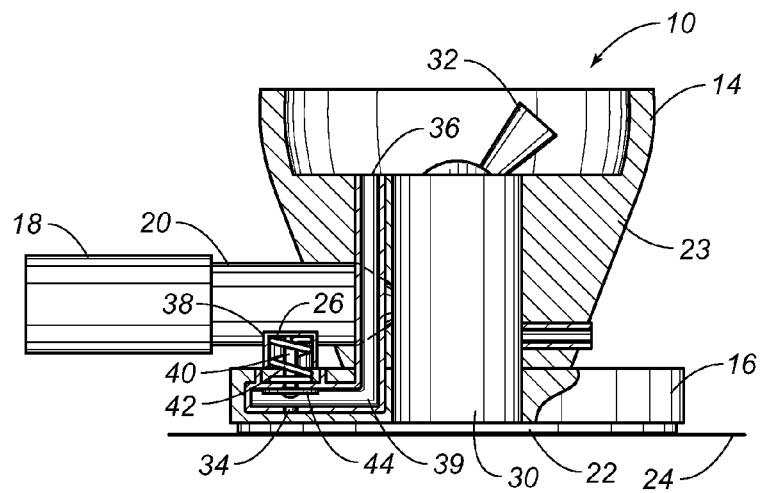
FIG. 2 is a side cross-sectional view showing the interior of the stethoscope of FIG. 1.

In FIG. 2, the interior of the stethoscope apparatus 10 of the present invention is particularly illustrated. In particular, a cylinder 30 is positioned within the interior of the head 14 so as to extend downwardly and have an end positioned slightly above the diaphragmatic surface 22 of the diaphragm 16. In particular, it can be seen that the tube 18 communicates with the interior of the cylinder 30 through the turret 20. A lever 32 is illustrated as extending outwardly of the cylinder 30. The lever 32 is suitable for causing the operation of the percussion portion of the present invention.

In FIG. 2, it can be seen that a sound pathway 77 opens to a wall of the head 14 (at air hole 78) so as to allow the excess air, sound, or pressure produced by the percussion apparatus to escape the cylinder 30. This serves to filter the percussion sound. It should be noted that the tube allows excess air, sound, or pressure from leaving the cylinder 30 but ideally does not allow sound to enter from the outside. In essence, it serves as a one way valve.

FIG. 2 particularly illustrates the percussion apparatus contained within the head 14 and extending to the diaphragm 16. As a result, the diaphragm deactivating device 26 is provided so as to temporarily deactivate the diaphragm as a means for filtering the sounds produced during auscultation and to increase the quality of the percussion sounds by allowing only sounds produced within the cylinder 30 from being transmitted by the tube 18 to the examiner. The turret 20 should be connected in such a manner that allows for simultaneous auscultation and percussion. A possible manner to connect the turret 20 may involve the rotational method used in traditional stethoscopes. The turret 20 may be directly connected to cylinder 30 (thus allowing percussion sounds to travel from cylinder 30 to tube 18) and may simultaneously allow access to air passageway 39 (thus allowing sound produced from the diaphragmatic surface 22 to travel to tube 18) while not allowing access to air passageway 37 (thus not allowing access to sound produced from bell 23). Since both the auscultation and percussion means have access to tube 18 simultaneously, a temporary deactivation of the diaphragm may be used to block auscultation sounds while using the percussion means. In this figure, it can be seen that the diaphragm deactivating device 26 includes a plunger 38 that is mounted on the top surface of the diaphragm 16. The plunger 38 includes a rod 40 supported by a spring 42. Spring 42 urges the plunger 38 into the upward position. As a result, the valve 44 allows air to flow freely through the air hole 34 and thus through the air passageway 39. When the plunger 38 is suitably depressed, the force of the spring 42 is overcome so that the valve 44 will reside over the air hole 34 and block air or sound from passing from the diaphragm surface 22 through the tube 18. The helical spring 42 will reactivate the diaphragm 16 after releasing pressure off the plunger 38 by returning the valve 44 to the home position (as illustrated in FIG. 2). The diaphragm deactivator device 26 is placed in such a position that allows for the temporary deactivation of the diaphragm 16 in a practical manner. Since, in percussion, it is necessary to press firmly on the body 24, the diaphragm deactivating device 26 may be located in such a manner that when the examiner presses firmly on the top of the diaphragm 16, the examiner will indirectly deactivate the diaphragm 16.

Figure 3:
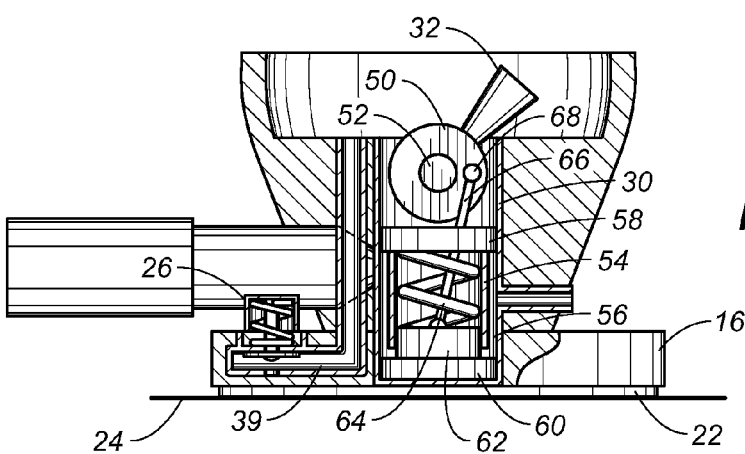
FIG. 3 is a side cross-sectional view of the stethoscope apparatus of the present invention showing the stethoscope in the auscultation position. The diaphragm surface is in first position and thus protrudes from the diaphragm. The percussion means does not make contact with the diaphragm during this stage. The plunger of the diaphragm deactivator is in first position and the piston is in the first position.

FIG. 3 illustrates the interior components of the cylinder 30. As noted, the cylinder 30 may be placed slightly above the diaphragmatic surface 22 so that during auscultation the entire surface of the diaphragm 16 will be used. This Figure shows that the lever 32 extends radially outwardly of a pulley 50. The pulley 50 is rotatably mounted on axle 52. As will be described hereinafter, the axle 52 will extend across the cylinder 30. An inner cylinder 54 is positioned within the interior of the cylinder 30 so as to define an annulus 56 through which air can pass and sound can be delivered directly from turret 20 and then to tube 18. The inner cylinder 54 extends concentrically with the outer cylinder 30. A fixation member 58 extends across the interior of the outer cylinder 30 so as to provide a support for the inner cylinder 54. The inner cylinder 54 will extend downwardly so that a lower end thereof is spaced from a rubber element 60 positioned above the diaphragmatic surface 22. Within the concept of the present invention, the rubber element 60 can be replaced by a diaphragmatic surface 22 that incorporates such element.

Importantly, a piston 62 is slidably received within the inner cylinder 54. A helical spring 64 has one end bearing against the surface of the fixation member 54 at an opposite surface connected to or bearing against the end of the piston 62. A flexible member 66, in the form of a wire, has one end 68 connected to a surface of the pulley 50 and an opposite end connected to the end 72 of piston 62. The flexible member 66 will extend downwardly through the interior of the fixation member 58 and through the interior of the spring 64.

The illustration of FIG. 3 shows the diaphragmatic surface 22 in its first position, the diaphragm deactivating device 26 in the first position, and the piston 62 in the first position so that auscultation procedures can be carried out. This figure shows the present invention in Phase 1.

Figure 4:
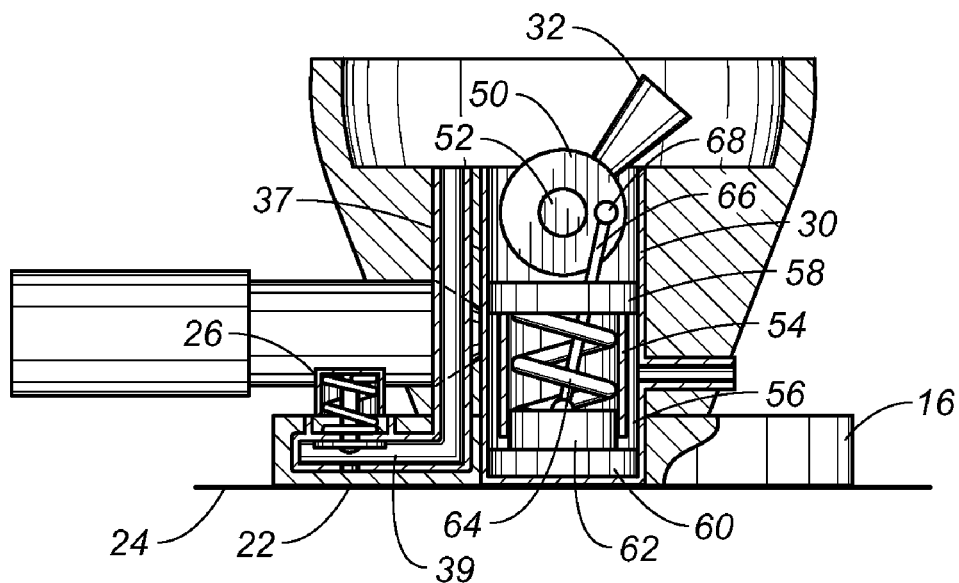
FIG. 4 is a cross-sectional view of the stethoscope apparatus of the present invention showing the diaphragmatic surface in the second position, the plunger of the diaphragmatic deactivator in the second position, and the piston in the first position. This illustrates the percussion means adjacent to the diaphragmatic surface and thus indirectly in contact with the body.

FIG. 4 shows the stethoscope apparatus 10 with the diaphragmatic surface 22 in the second position, plunger 38 in the second position and the piston 62 in the first position (Phase 2). The diaphragm deactivating device 26 is illustrated as depressed (second position) so as to block air hole 34 and thus block sound from diaphragm 16 from accessing air pathway 39.

Figure 5:
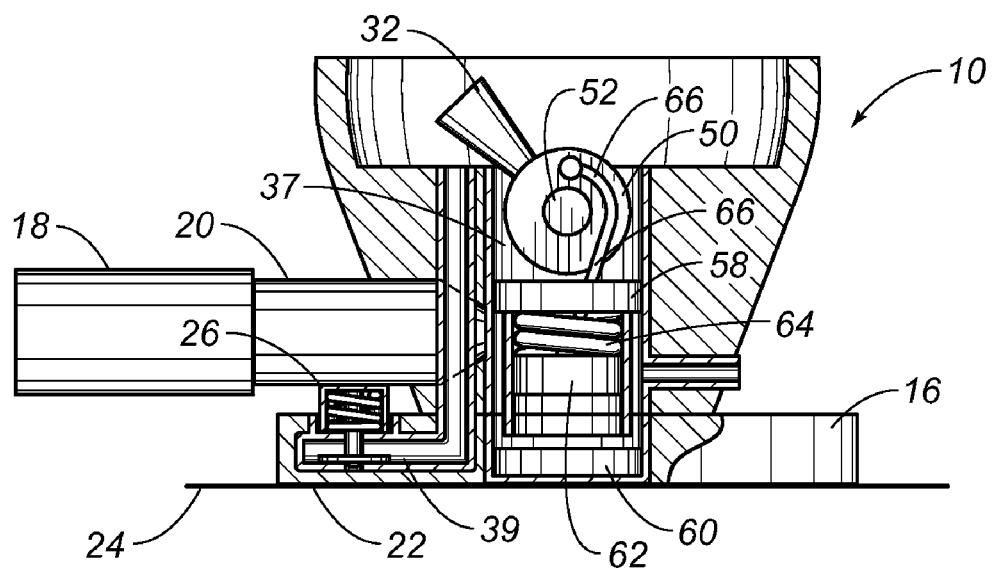
FIG. 5 is a side cross-sectional view of the stethoscope apparatus of the present invention showing the stethoscope with diaphragmatic surface in the second position, the plunger of the diaphragmatic deactivator in the second position, and the piston in the second position.

FIG. 5 shows the stethoscope apparatus 10 with the diaphragmatic surface 22 in the second position, plunger 38 in the second position, and piston 62 in the second position (Phase 3). As can be seen, the lever 32 is rotated such that the pulley 50 causes the flexible member 66 to rotate therewith about the axle 52. As a result, the spring 64 will compress between the fixation member 58 and the piston 62. The piston 62 is moved away from the rubber element 60. The flexible member 66 causes the piston 62 to displace from its first ("home") position.

FIG. 4 further shows the stethoscope apparatus 10 in Phase 4. In this Phase, the diaphragmatic surface 22 in the second position, the plunger 38 in the second position, and piston 62 in the first position. The figure illustrates that when the lever 32 is released, the pulley 50 will rotate about the axle 52 by the action of the helical spring 64. The force exerted by the helical spring 64 will urge the piston 62 downwardly toward the rubber element 60. Since the percussion means is adjacent to the diaphragmatic surface 22 during this phase, a force of percussion will pass through the diaphragmatic surface 22 onto the body 24 and the sound produced from the impact of the piston 62 and the rubber element 60 will resonate within the annulus 56 and travel to tube 18 via turret 20. The excess sounds may escape via air passageway 77. As the piston 62 is forced back to its "home" position, it pulls the flexible wire 66 along with it and also brings the lever 32 back to its original forward position.

Figure 6:
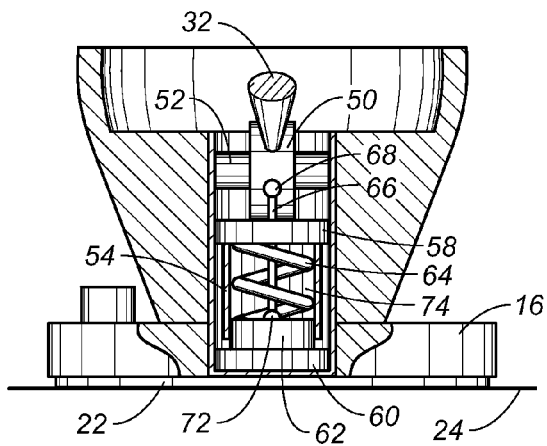
FIG. 6 shows a front cross-sectional view of the stethoscope showing of the present invention showing the diaphragmatic surface in the first position, the plunger of the diaphragmatic deactivator in the first position, and the piston in the first position.

In FIG. 6, the stethoscope apparatus 10 is shown in front view. The apparatus 10 is shown with the diaphragmatic surface 22 in the first position, plunger 38 in the first position, and the piston 62 in the first position. It can be seen that the flexible wire 66 is connected to the pulley 50 through the wire attachment point 68. The flexible wire 66 is connected to the piston 62 by wire attachment point 72. In this arrangement, the piston 62 is free to slide through the interior 74 of the inner cylinder 54. In essence, this movement parallels that of a spring-loaded apparatus. As the examiner pulls back on the lever 32, a force is generated. By releasing the lever 32, the force is released and everything returns to its original position.

Figure 7:
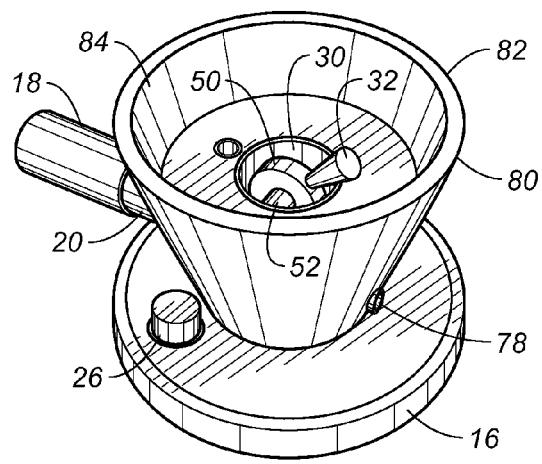
FIG. 7 is a top perspective view showing the rotation of the stethoscope apparatus as contained within the head of the stethoscope. The lever is in the first position.

FIG. 7 illustrates a top perspective view of the stethoscope apparatus 10 of the present invention. As can be seen, the diaphragm 16 is located at the bottom end of bell 23. An air hole 78 opens to the side of the bell 23. The deactivator switch 26 is located along the top surface 28 of the diaphragm 16 in a suitable position for easy operation by the finger of the examiner. The bell 23 has a top edge 82 and a recessed area 84. The lever 32 will extend upwardly through the interior of the cylinder 30 but within the upper edge 82 of the recessed area 84 of bell 23. It can be seen that the lever 32 extends radially outwardly of the pulley 50. The pulley 50 is rotatably mounted on the axle 52 extending across the cylinder 30. Any sound from the percussion apparatus of the present invention will pass through the turret 20 to the tube 18 and the ears of the examiner. The excess sounds produced from within the cylinder 30 will escape via air hole 78 which leads to the outside. The passageway between cylinder 30 and air hole 78 serves as a one-way valve by allowing sound to exit from cylinder 30 but not allowing sound to enter cylinder 30 from the outside.

Figure 8:
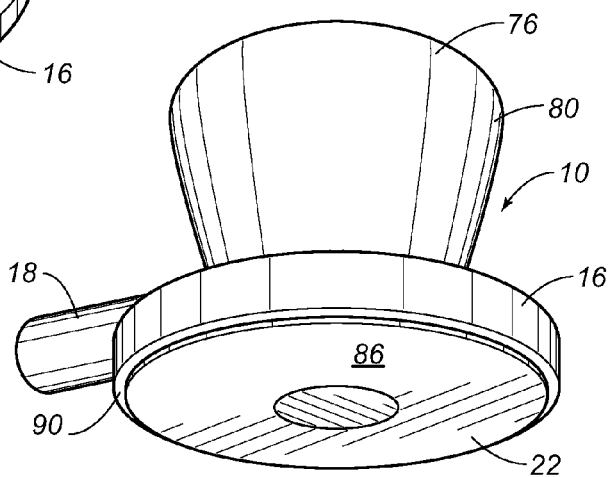
FIG. 8 is a bottom perspective view of the stethoscope showing the central surface beneath the percussion apparatus.

FIG. 8 shows the bottom perspective view of the stethoscope apparatus of the present invention. As can be seen, the diaphragmatic surface 22 extends slightly below the bottom edge 90 of the diaphragm 16. The rubber surface element 86 is part of the diaphragmatic surface 22 and is located at the center of the diaphragmatic surface 22. The bell 23 of the housing 80 extends upwardly in a rather frustoconical configuration from the diaphragm 16. Tube 18 is attached to the turret 20 and extends outwardly from the head 14.

As with many stethoscopes, the diaphragmatic surface 22 is placed on the diaphragm via rubber and elastic material that allows for the movement of the diaphragmatic surface 22. As the examiner presses down firmly on the diaphragm 16, the diaphragmatic surface 22 will naturally elevate and thus the percussion means will come into contact with the diaphragmatic surface 22. As noted above, by pressing firmly on the diaphragm 16, temporary deactivation of the diaphragm 16 is simultaneously achieved. Various modifications may be made respect to the diaphragmatic surface 22. The diaphragmatic surface may be modified such that the center of the diaphragmatic surface 86 is made of rubber or some other material so as to receive the impact from the piston 62. Also, the diaphragmatic surface 22 may be further depressed centrally to accommodate the percussion means and thus limit the area of diaphragmatic surface 22 in contact with the body during percussion. In a further variation, the diaphragmatic surface may be in the shape of ring and thus empty in the center to allow rubber element 60 of the percussion means to be in direct contact with the body 24.

The percussion apparatus of the present invention is described as being centrally located within the diaphragm side of the stethoscope head; however, it does not have to be centrally located. In designs where the percussion means is not centrally located within the head, the air holes 34 and 36 corresponding to the diaphragm 16 and bell 23, respectively, may then be centrally located. Furthermore, the percussion apparatus may be placed on any side of the head (either the bell side or the diaphragm side), may have a separate side on the head by adding an extra side to the traditional stethoscope (such as in a triple head stethoscope), may be attached to the head, or may be a separate entity with an additional tube extending to it.

In present invention, if the percussion apparatus is contained within the bell 23 of the stethoscope 10, a bar may be placed on the opening surface of the bell 23 to prevent tapping directly on the body 24.

It should be noted that utilizing a separate head merely for the purpose of percussion may be less complex than the preferred embodiment of the present invention. Such a design may eliminate the need for temporary deactivation of the diaphragm or bell and would still allow for quality percussion sounds.

In alternative embodiments, the percussion apparatus may descend by an activation switch and/or the diaphragm 16 may be made as a movable segment.

In the configuration of the present invention, the percussion apparatus may be detached from the head 14 via a release switch or other method and used separately as a separate apparatus. The examiner may trigger the apparatus in the same way as when the apparatus is contained within head 14 of the stethoscope 12. The sounds emitted from the percussion apparatus may be loud and clear enough to be interpreted by the examiner without the use of the stethoscope, however, a stethoscope may be used to enhance the sounds so as to parallel auscultatory percussion.

While performing auscultatory percussion, the stethoscope head 14 may have an additional air passageway extending from the turret 20 and leading to the outside of the head (or there may be an additional tube connecting tube 18 to the percussion apparatus) and thus allowing the examiner to appreciate both the indirect sounds (namely those sounds that echo from within the body and are thus transmitted by the diaphragm 16 or the bell 23) and direct sounds (impact sounds from the percussion apparatus).

When percussing at a distance from the diaphragmatic surface 22, it is important to note that the sounds produced do not correspond to the area beneath head 14 of the stethoscope 10.

In the preferred embodiment, the lever 32 should not extend beyond the top edge 82 of the bell 23. In stethoscope designs where the lever 32 would extend beyond the top edge of the bell 23, the lever 32 must be removed when utilizing the bell 23. The lever 32 may be removed by a simple counterclockwise rotation in the manner of removing a screw. As such, the lever 32 can also be replaced by a clockwise rotation in the manner of replacing a screw. Depending on the finger size of the examiner, it may be practical to have the lever 32 that exceeds the top edge 82 of the bell 23. In alternative embodiments, the lever 32, or other switch, may be placed on the side of the stethoscope head 12 or in some other location and not necessarily be confined within the recessed area 84 of the bell 23. It should be noted that within the broad concept of the present invention, the percussion apparatus may utilize a switch such as a plunger, a rotational lever, or other means capable of triggering the percussion apparatus. It should also be noted that the percussion means may be mechanical or electrical and may utilize a spring loaded system, hydraulics, or other means capable of producing an impact comparable to manual percussion.

It should be noted that it is possible that the present invention be formed with electronics. For example, such electronics can allow for the automatic percussion and may be set to multiple taps. The taps may be in such a manner that the piston 60 drops and immediately rises back to the top so as to mimic manual percussion. The electrical form of the present invention may combine the functions of both the percussion apparatus and the temporary deactivator of the diaphragm. In the electronic form, the stethoscope may be connected to a device capable of recording and converting the sounds to digital format. Such devices have built-in software capable of providing a differential diagnosis based on auscultation. Since the present invention provides a stethoscope that is capable of producing both auscultation and percussion sounds, software may be designed to compare the sounds of both auscultation and percussion and thus provide a more accurate differential diagnosis.

In general, the more in sync the percussion apparatus and temporary deactivator of the diaphragm are, the more simultaneous the method of auscultation and percussion becomes. To be completely simultaneously, the examiner simply does not press on the temporary deactivator switch 26. Without the temporary deactivation of the diaphragm, the examiner may hear excess sounds that may or may not be warranted. In configurations of the present invention where the diaphragm 16 is not intended to be deactivated, it is possible to have a modified diaphragmatic surface 22 (as discussed previously) that is ring-shaped and thus empty in the center in order to allow the bottom of the percussion apparatus to have direct contact on the body.

Thus, any device contained within the head of the stethoscope or attached to some part of the stethoscope and capable of producing a tap similar to that of manual percussion serves the purpose of the present invention.

In the method of the present invention, the examiner should carry out several steps. First, the examiner should place the diaphragm 16 (in particular the diaphragmatic surface 22) flat on the body 24 and listen to the auscultatory sounds produced by the diaphragmatic surface 22. On the stethoscopes that incorporate both the diaphragm and the bell on the same side, the examiner may first listen to lower frequency sounds produced by the bell and then may press down slightly on the diaphragm 16 and listen to the higher frequency sounds produced by the diaphragm. Secondly, the examiner should press down firmly on the diaphragm 16 in such a manner that the thumb or another finger directly presses on the plunger 38 of the deactivator 26 and thus brings the plunger 38 to the second position. The pressure should be enough to not only elevate the diaphragmatic surface 22 to the second position (to the point where it makes contact with the bottom of cylinder 30), but also to temporary deactivate the diaphragm 16 (by blocking the air hole 34). Thirdly, while maintaining this pressure on the diaphragm 16, the examiner should pull back on the lever 32 to the desired point with the index finger and then let go of the lever. This produces the percussion sound and also returns the lever to its first position. As the examiner removes the stethoscope from the body, naturally the diaphragmatic surface 22 will return to its first position and the plunger 38 will return to its first position via the spring 42. This process may be repeated as necessary. As a result, the percussion sounds is transmitted to the examiner in a clean and amplified manner. Additionally, the examiner is able to perform simultaneous auscultation and percussion.

The foregoing disclosure and description of the invention is illustrative and explanatory thereof. Various changes in the details of the illustrated construction can be made within the scope of the appended claims without departing from the true spirit of the present invention. The present invention should only be limited by the following claims and their legal equivalents.

I claim:

1. An apparatus for auscultation and percussion of a body comprising:
   a stethoscope having a head, said head having a diaphragm on one side thereof, said stethoscope having a tube extending to said head; and
   a percussing means positioned in said head, said percussing means for selectively producing a percussion against the body such that a sound from the percussion is passed through said tube from said head, said percussing means for producing an impact against a surface, said percussing means comprising:
      a cylinder positioned within said head and extending to a point slightly above said diaphragm;
      a piston slidably positioned within said cylinder; and
      an activating means connected to said piston, said activating means for moving said piston between a first position adjacent an impact element and a second position away from said impact element, said diaphragm having a surface formed thereon suitable for being placed against the body, said activating means comprising:
         a lever rotatably mounted in said head;
         a flexible member affixed to said lever at one end and affixed to said piston at an opposite end; and
         a spring extending in said cylinder and connected to said piston so as to urge said piston toward said first position.

2. The apparatus of claim 1, further comprising:
   a diaphragm deactivating means affixed to said head for selectively deactivating said diaphragm.

3. The apparatus of claim 2, said diaphragm deactivating means comprising:
   a plunger resiliently mounted on a surface of said head; and
   an air hole suitable for transmitting sound from said diaphragm to said tube, said plunger movable between a first position opening said air hole and a second position blocking said air hole.

4. The apparatus of claim 1, said cylinder comprising:
   an outer cylinder; and
   an inner cylinder positioned interior of said outer cylinder so as to define an air passage in an annulus therebetween, said piston being slidably received within said inner cylinder, said spring extending through said inner cylinder, said lever positioned within said outer cylinder, said flexible member extending from said lever through an interior of said spring.

5. The apparatus of claim 4, said activating means further comprising:
   an axle extending across said outer cylinder, said lever having a pulley rotatably mounted to said axle, said lever extending radially outwardly of said pulley; and
   a fixation member extending across said outer cylinder, said inner cylinder affixed to said fixation member on a side opposite said lever, said spring having an end bearing against said fixation member.

6. The apparatus of claim 5, said flexible member being a wire having a one end affixed to a surface of said pulley and an opposite end affixed to a surface of said piston opposite said surface of said impact element.

7. The apparatus of claim 1, said head having a bell extending upwardly from said diaphragm, said bell having a recessed area formed inwardly of an outer edge at an end opposite said diaphragm, said lever extending into said recessed area and inwardly of said outer edge of said bell.

8. The apparatus of claim 1, said diaphragm having a diaphragmatic surface, said diaphragmatic surface movable between an inward position and an outward position of said diaphragm, said diaphragmatic surface having a rubber surface means positioned centrally thereof, said percussing means being adjacent to said rubber surface means while said diaphragmatic surface is in said inward position.

9. The apparatus of claim 4, said inner cylinder having an edge opposite said lever positioned in spaced relation to said surface of said impact element.

10. A percussion apparatus comprising:
    a housing having a surface suitable for positioning against a body;
    a cylinder extending through the interior of said housing so as to have an end slightly above said surface;
    a piston located within said cylinder;
    an impact element; and
    an activating means cooperative with said piston, said activating means for moving said piston between a first position adjacent to said impact element and a second position away from said impact element, said activating means comprising:
       a lever rotatably mounted within said housing;
       a flexible member affixed to said lever at one end and affixed to said piston at an opposite end; and
       a spring extending in said cylinder and connected to said piston so as urge said piston toward said impact element.

11. The apparatus of claim 10, said surface being a diaphragmatic surface having a rubber surface means positioned generally centrally thereof, said cylinder adjacent to said rubber surface means when said piston is in said second position.

12. The apparatus of claim 10, said cylinder comprising:
    an outer cylinder; and
    an inner cylinder positioned interior of said outer cylinder so as to define an air passage in an annulus therebetween, said piston being slidably received within said inner cylinder, said spring extending through said inner cylinder, said lever positioned within said outer cylinder, said flexible member extending from said lever through an interior of said spring, said inner cylinder having an edge opposite said lever positioned in spaced relation to said impact element.

13. The apparatus of claim 12, said activating means comprising:
    an axle extending across said outer cylinder, said lever having a pulley rotatably mounted to said axle, said lever extending radially outwardly of said pulley; and
    a fixation member extending across said outer cylinder, said inner cylinder affixed to said fixation member on a side opposite said lever, said spring having an end bearing against said fixation member.

14. The apparatus of claim 10, said housing comprising:
a bell; and
a diaphragm affixed to an end of said bell, said diaphragmatic surface extending across a side of said diaphragm opposite said bell, said cylinder being in fluid communication with an air hole of said diaphragm and an air hole of said bell, said cylinder having a one way valve extending from said cylinder to outside said housing.

15. The apparatus of claim 10, further comprising:
a tube in fluid communication with an interior of said housing such that a sound produced by the impact of said piston passes outwardly of said housing through said tube.

* * * * *